United States Patent [19]

Esser et al.

[11] Patent Number: 5,851,515

[45] Date of Patent: Dec. 22, 1998

[54] ANTIPERSPIRANT COMPOSITION

[75] Inventors: Isabelle Claire Esser, Merseyside; Shirley Jones, Leeds; Steven Wigglesworth, West Yorkshire, all of United Kingdom

[73] Assignee: Helene Curtis, Inc., Chicago, Ill.

[21] Appl. No.: 804,870

[22] Filed: Feb. 24, 1997

[30] Foreign Application Priority Data

Feb. 29, 1996 [GB] United Kingdom .................. 9604341

[51] Int. Cl.$^6$ .............................. A61K 7/32; A61K 7/34; A61K 7/36; A61K 7/38
[52] U.S. Cl. ................ 424/65; 424/66; 424/67; 424/68; 424/400; 424/401
[58] Field of Search ................. 424/65, 66, 67, 424/68, 400, 401

[56] References Cited

U.S. PATENT DOCUMENTS

| | | | |
|---|---|---|---|
| 4,435,382 | 3/1984 | Shin et al. | 424/66 |
| 4,777,034 | 10/1988 | Olivier et al. | 424/65 |
| 5,135,741 | 8/1992 | Park | 424/66 |
| 5,292,530 | 3/1994 | McCrea et al. | 424/66 |

FOREIGN PATENT DOCUMENTS

| | | |
|---|---|---|
| 0 000 604 | 2/1979 | European Pat. Off. . |
| 0 028 853 | 5/1981 | European Pat. Off. . |
| 0 059 882 | 9/1982 | European Pat. Off. . |
| 0 275 695 | 7/1988 | European Pat. Off. . |
| 0 291 334 | 11/1988 | European Pat. Off. . |
| 0 295 071 | 12/1988 | European Pat. Off. . |
| 0 310 252 | 4/1989 | European Pat. Off. . |
| 0 312 270 | 4/1989 | European Pat. Off. . |
| 0 318 206 | 5/1989 | European Pat. Off. . |
| 1 192 021 | 5/1970 | United Kingdom . |
| 501 862 | 2/1978 | United Kingdom . |
| 2 043 445 | 10/1980 | United Kingdom . |
| 84/02262 | 6/1984 | WIPO . |

OTHER PUBLICATIONS

GB Search Report GB 9604341.9 Apr. 26, 1996.
GB Search Report GB 9612945.7 Aug. 27, 1996.

*Primary Examiner*—Shelley A. Dodson
*Attorney, Agent, or Firm*—Milton L. Honig

[57] ABSTRACT

An antiperspirant composition comprising 10 to 70% by weight ethanol, a thickener in an amount up to 1%, 5 to 20% by weight of an antiperspirant active and up to 5% by weight of an emollient.

12 Claims, No Drawings

ANTIPERSPIRANT COMPOSITION

BACKGROUND OF THE INVENTION

1. Field of the Invention

The invention relates to an antiperspirant composition, and more particularly to an alcoholic antiperspirant composition for use with big ball roll-on dispensers.

2. The Related Art

Antiperspirant compositions are utilised in many physical forms e.g. roll-ons, creams, aerosols and pump sprays. Roll-on antiperspirant formulations are particularly efficient and popular. Roll-on dispensers are of two main types, namely standard ellipsoid roll-ons and "big ball" roll-ons.

Ellipsoid packs are well known in the art, and comprise a rotatable ball having a diameter of approximately 2.5 cm. Ellipsoid roll-ons generally contain alcohol based antiperspirant formulations.

Big ball roll-ons typically have a rotatable ball typically having a diameter of 3.5 cm. Big bail roll-on packs were originally designed for non-alcohol based formulations such as silicone emulsions. Big ball roll-on containers are popular due to increased comfort in-use, increased ease of use, easier application, better body fit and ease of dosing.

However, a disadvantage of big ball roll-on packs is the tendency of antiperspirant formulations to form a crust-like deposit (crusting) on the ball following use. Crusting on the surface of the big ball is partly due to the increased surface area of such big balls in comparison with ellipsoid packs, which can lead to greater drying out of material on the big ball surface.

Crusting or deposition of antiperspirant formulations on the big ball results in jamming of the ball, thereby hindering rotation of the ball, Alcohol based formulations are particularly unsuitable for use in big ball containers due to extreme crusting/jamming. More particularly, the alcohol present in the formulation flashes off from big ball surfaces to leave a deposit of antiperspirant active crystals on the surface thereby resulting in crusting and/or jamming.

An object of the invention is to provide an alcohol based antiperspirant formulation suitable for use with a big ball container.

SUMMARY OF THE INVENTION

According to the invention there is provided an antiperspirant composition comprising 10 to 70% by weight ethanol, a thickener in an amount up to it, 5–20% by weight of an antiperspirant active and up to 5% by weight of an emollient. Preferably, the ethanol is present at 30–60% by weight of the composition.

Suitably, the antiperspirant composition comprises 0.3 to 0.8% thickener. Preferably, the thickener is a cellulose thickener.

Suitably, the antiperspirant composition comprises 15 to 20% antiperspirant active. Preferably the antiperspirant comprises 0.2 to 2% by weight emollient.

Advantageously, the emollient comprises a mixture of PPG-15 stearyl ether, cyclomethicone and propylene carbonate, and may be present at a level of 0.1–5%.

According to a second aspect of the invention an alcohol based antiperspirant system is provided comprising a big-ball roll-on hand held package, the package being in a form suitable for use as a hand held applicator, said big ball having a diameter of from about 3.0 to 4.0 cm and an antiperspirant composition having an effective amount of an antiperspirant active, an effective amount of a thickener and an effective amount of an emollient.

According to a further aspect of the invention there is provided use of an emollient in the preparation of an alcohol based antiperspirant composition to prevent jamming of a big ball roll-on applicator. Surprisingly the emollient improves the sensory properties of the formulation is whilst simultaneously substantially eliminating crushing and/or jamming.

DETAILED DESCRIPTION OF THE INVENTION

The present invention addresses the problem of crusting and jamming of alcoholic based antiperspirant formulations in big ball applicators. A combination of an emollient and minimal levels of thickener in the presence of antiperspirant actives results in a formulation with significantly improved jamming and crusting properties.

Packages for compositions according to the invention may have a rollball which has a diameter greater than 3 cm, and conveniently is between 3 and 5 cm, more preferably 3 and 4 cm diameter. Compositions according to the invention are alcoholic, and have the antiperspirant active in solution.

Although the applicant does not wish to be bound by any specific theory, it is believed that a synergy exists between the antiperspirant active and thickeners used in alcohol based antiperspirant formulations which results in crusting and jamming. The combination of thickener and active results in more severe crusting and/or jamming than the presence of either ingredient alone.

Surprisingly, it has been observed that (1) an alcoholic solution with 0.8% cellulose thickener and no antiperspirant active results in no jamming, (2) an alcoholic solution of antiperspirant active and no thickener gives slight crusting while (3) the combination of a high level of thickener (e.g. 0.8%) and antiperspirant active (e.g. 17.5%) gives an unacceptable degree of crusting and jamming of the big ball.

Cosmetic grade ethanol is preferred for use in the formulations of the invention. Ethanol can be used at levels of 10 to 70%, preferably 30 to 60% and most preferably 50–60%.

The thickener used in the formulations of the invention is suitably a cellulosic thickener or any other thickener which can thicken an acid antiperspirant solution. An example of a suitable cellulosic thickener is Klucel M (a hydroxypropyl cellulose).

The antiperspirant active used in the formulations of the invention can be any classified antiperspirant active such as activated aluminium chlorohydrate, aluminium chlorohydrate, aluminium pentchlorhydrate, aluminium zirconiumchlorhydrate and other actives known in the art. The antiperspirant active should be in solution and present in the formulation at a level of 5 to 20% by weight, preferably, 10 to 20% and most preferably 15 to 20%.

The emollient used in the formulation of the invention is preferably a cyclomethicone combined with PPG-15 stearyl ether and propylene glycols although many other emollients known in the art may also be suitable.

In a preferred formulation, cyclomethicone is present at a level of up to 5%, more preferably 0.2 to 2%, PPG-15 stearyl ether at a level of up to 5% and more preferably 1 to 3% while propylene glycol is present at preferably levels of up to 5% and more preferably 1.5 to 4.5%.

The thickener used in the formulations of the invention dictates the viscosity of the antiperspirant compositions.

Suitably, the thickener is present at a level sufficient to impart a viscosity of up to 2500 cps to the antiperspirant composition, preferably 100 to 1500 cps and most preferably 100 to 900 cps. The viscosity of the composition is balanced with the need to minimise the level of thickener in the composition to avoid crusting or jamming. Accordingly, the level of thickener is selected to provide a balance between the minimum required to give acceptable sensory properties and viscosity and the maximum permitted to give minimal or no crusting and/or jamming.

The invention will now be described having regard to the following non-limiting examples:

EXAMPLE 1

| Ingredient | % w/w |
|---|---|
| Ethanol (carrier) | 57.6% |
| Hydroxypropylcellulose (thickener) | 0.4% |
| Aluminium zirconium pentachlorhydrate (antiperspirant active) | 17.5% |
| Perfume | 1% |
| Cyclomethicone (emollient, anti-tacking agent) | 1% |
| PPG-15 stearyl ether (crystallization inhibitor, emollient) | 2% |
| Propylene glycol (as above/humectant) | 3% |
| Water (solvent/carrier) | 17.5% |
| TOTAL | 100% |

The above ingredients were mixed in a homogeneous fashion according to standard methods known in the art.

EXAMPLE 2

In a comparative test, the composition of example 1 was tested in a panel test in which the incidence of blocking of the container was assessed against commercially available antiperspirant lotion formulations which contained no emollients (as is a feature of this invention) in containers with different size roll balls.

It was found that the commercially available formulation in a pack with a 2.5 cm diameter spherical roll ball had an incidence of blocking of 6.5%, and the same formulation in a pack having a 3.5 cm diameter roll ball had a blockage incidence of 16%. However, the formulation of example 1 in a pack having a ball diameter of 3.5 cm had an incidence of blocking of only 3.5%. In addition to the crusting benefit described above, compositions according to the invention were also found to have benefits in terms of reduced skin irritation.

EXAMPLE 3

In a further in vitro comparative test, samples of the commercially available antiperspirant lotion and the composition tested in Example 2 were packaged in packs having a 3.5 cm diameter rollball, and stored at ambient and elevated temperature conditions for a period of up to 30 days. The tests involved storing the packs both upright and at angles, and assessing them regularly. In these tests, even after 30 days the compositions according to the invention, in particular having the levels of emollient and thickener according to the invention, were found to have either no or very slight levels of crusting, whereas even after as little as 5 days the commercially available formulations in the "big ball" packs were found to have slight and moderate levels of crusting, which worsened as the test progressed.

We claim:

1. An antiperspirant comprising 10 to 70% by weight ethanol, a thickener in an amount up to 1%, 5 to 20% by weight of an antiperspirant active and 0.1 to 5% by weight of an emollient.

2. An antiperspirant composition according to claim 1 packaged in a container having a rollball with a diameter of at least 3 cm.

3. An antiperspirant composition according to claim 2 wherein the rollball has a diameter of between 3 and 5 cm.

4. An antiperspirant composition according to claim 1 wherein said composition comprises 30 to 60% ethanol.

5. An antiperspirant composition according to claim 1, wherein said composition comprises 0.3 to 0.8% by weight thickener.

6. An antiperspirant composition according to claim 1, wherein said composition comprises 0.2 to 2 by weight emollient.

7. An antiperspirant composition according to claim 1 wherein said composition comprises 15 to 20% antiperspirant active.

8. An antiperspirant composition according to claim 1 wherein said composition thickener is a cellulosic thickener.

9. An antiperspirant composition according to claim 1 wherein the emollient comprises a mixture of PPG-15 stearyl ether, cyclomethicone and propylene glycol.

10. An antiperspirant system comprising:

(a) a big-ball roll-on hand held package, the package being a hand held applicator, said big ball having a diameter of from about 3.0 to 4.0 cm and (b) an antiperspirant composition comprising 10 to 70% by weight ethanol, an effective amount of an antiperspirant active, an effective amount of a thickener and an effective amount of an emollient.

11. An antiperspirant composition according to claim 1 wherein the emollient is a silicone.

12. An antiperspirant composition according to claim 11 further comprising from 1.5 to 5% of propylene glycol.

* * * * *